United States Patent
Hersh et al.

(10) Patent No.: US 11,406,531 B1
(45) Date of Patent: Aug. 9, 2022

(54) METHOD FOR THE AMELIORATION OF ECTATIC AND IRREGULAR CORNEAL DISORDERS

(71) Applicants: Peter S. Hersh, Teaneck, NJ (US); Steven A. Greenstein, Teaneck, NJ (US); John D. Gelles, Teaneck, NJ (US)

(72) Inventors: Peter S. Hersh, Teaneck, NJ (US); Steven A. Greenstein, Teaneck, NJ (US); John D. Gelles, Teaneck, NJ (US)

(*) Notice: Subject to any disclaimer, the term of this patent is extended or adjusted under 35 U.S.C. 154(b) by 0 days.

(21) Appl. No.: 17/528,484

(22) Filed: Nov. 17, 2021

Related U.S. Application Data

(60) Provisional application No. 63/225,484, filed on Jul. 24, 2021.

(51) Int. Cl.
*A61F 9/007* (2006.01)
*A61B 3/107* (2006.01)
(Continued)

(52) U.S. Cl.
CPC ........... *A61F 9/007* (2013.01); *A61B 3/0025* (2013.01); *A61B 3/107* (2013.01); *A61F 2/147* (2013.01)

(58) Field of Classification Search
CPC .......... A61F 2009/00872; A61F 9/0079; A61F 9/00831; A61F 2/142; A61F 9/008;
(Continued)

(56) References Cited

U.S. PATENT DOCUMENTS

| 8,394,140 B2 * | 3/2013 | Chapoy ............... A61F 2/147 623/5.11 |
| 8,409,177 B1 | 4/2013 | Lai |

(Continued)

OTHER PUBLICATIONS

Nubile et al., "Epithelial and stromal remodelling following femtosecond laser—assisted stromal lenticule addition keratoplasty (SLAK) for keratoconus" Sci Rep 11, 2293 (2021).

*Primary Examiner* — Brandi N Thomas
(74) *Attorney, Agent, or Firm* — RosserIP, LLC; Roy Rosser (57) ABSTRACT

Methods for the amelioration of ectatic corneal disorders using corneal augmentations are disclosed. The shape of the augmentation is determined using data obtained from mapping of a patient's cornea based on computerized corneal topography and tomography. Factors considered include the maximum keratometry and specific iso-deviation contours. In one embodiment, an augmentation is inlayed into a femtosecond created, intrastromal pocket. In a further embodiment, an onlay augmentation is positioned over a region of the cornea from which the epithelial layer has been removed. The onlay is held in place by glue, sutures, tucking under a perimeter chamfer, or some combination thereof, until the epithelial layer regrows over the augmentation. In a further embodiment, the inlay or only augmentation is followed by a post-augmentation, further reshaping of the corneal augmentation. In one embodiment, this further reshaping is photorefractive keratectomy (PRK) surgery. In another and a phototherapeutic keratectomy (PTK) surgery.

20 Claims, 7 Drawing Sheets

(51) Int. Cl.
*A61B 3/00* (2006.01)
*A61F 2/14* (2006.01)

(58) Field of Classification Search
CPC .. A61F 2/1451; A61F 9/0017; A61F 9/00781; A61F 9/0081; A61F 9/00834; A61F 2/148; A61F 2009/0087; A61F 9/00804; A61F 9/00825; A61F 2/145; A61F 2/147; A61F 2009/00848; A61F 2009/00887; A61F 9/00802; A61F 9/00827; A61F 9/00836; A61F 2/15; A61F 2009/00842; A61F 2009/00891; A61F 2009/00893; A61F 2250/0067; A61F 9/00736; A61F 9/00812; A61F 9/00814; A61F 9/009; A61F 2/0077; A61F 2/1453; A61F 2/1635; A61F 2/1662; A61F 2002/0081; A61F 2002/1699; A61F 2009/0052; A61F 2009/00844; A61F 2009/00853; A61F 2009/00868; A61F 2009/00897; A61F 2210/0085; A61F 2220/0008; A61F 2240/004; A61F 2250/0001; A61F 2250/0091; A61F 9/00; A61F 9/007; A61F 9/013; A61B 3/103; A61B 3/14; A61B 3/16; A61B 17/28; A61B 18/20; A61B 2090/064; A61B 2560/0219; A61B 2560/063; A61B 2562/0247; A61B 3/0083; A61B 3/10; A61B 3/107; A61B 34/72; A61B 5/0071; A61B 5/03; A61B 5/076; A61B 5/4839; A61B 5/6821; A61B 90/06

See application file for complete search history.

(56) References Cited

U.S. PATENT DOCUMENTS

| | | | |
|---|---|---|---|
| 9,931,199 | B2 | 4/2018 | Albertazzi |
| 10,881,503 | B2 * | 1/2021 | Peyman .................. A61F 2/145 |
| 10,914,746 | B2 * | 2/2021 | Lema Gesto .......... G01N 33/53 |
| 10,973,685 | B2 * | 4/2021 | Dai ..................... A61F 9/00817 |

* cited by examiner

SECTION ON "BB"
FIG. 7 B

SECTION ON "BB"
FIG. 7 C

METHOD FOR THE AMELIORATION OF ECTATIC AND IRREGULAR CORNEAL DISORDERS

CROSS-REFERENCE TO RELATED APPLICATIONS

This is a US non-provisional patent application claiming priority to U.S. provisional patent application No. 63/225,484 entitled "Method for Treatment of Keratoconus" that was filed on Jul. 24, 2021, the contents of which are hereby fully incorporated by reference.

BACKGROUND OF THE INVENTION

(1) Field of the Invention

The invention relates to methods for the amelioration of ectatic and irregular corneal disorders and more particularly to the use of corneal augmentations as either inlays or onlays as a means to ameliorate ectatic corneal disorders such as, but not limited to, keratoconus.

(2) Description of Related Art

Corneal ectasia is a result of the thinning and subsequent distortion of the cornea. This distortion alters the normal optical anatomy of the cornea and decreases vision. Corneal ectasia may have several causes and may manifest as a condition such as, but not limited to, keratoconus, pellucid marginal degeneration and keratoglobus. Corneal ectasia may also be iatrogenic in nature resulting from various surgeries such as, but not limited to, laser-assisted in-situ keratomileusis (LASIK), small incision lenticule extraction (SMILE), and photorefractive keratectomy (PRK).

The most common natural manifestation of corneal ectasia is keratoconus, a condition that occurs in approximately 1 in 2000 individuals. This is an asymmetric corneal ectatic disorder characterized by progressive corneal protrusion and thinning, typically causing irregular astigmatism and impaired visual function. In particular, the normally dome, or spherically, shaped cornea becomes distorted resulting in the formation of a cone shaped bulge. This cone shaped protrusion typically adversely affects vision.

Methods of ameliorating corneal ectasia depend on the type and severity of the condition and include treatments such as, but not limited to contact lenses, intra corneal implants, cross-linking and a corneal transplant.

Intra-corneal implants include intrastromal corneal ring segments (ICRS) made of materials such as, but not limited to, PMMA. In the US, these are often referred as Intacs®, which is the tradename of the devices produced by Addition Technology, Inc. of Lombard Ill., a subsidiary of AJL Ophthalmic, a Spanish company headquartered in Minano, Alva, Spain. One shortcoming of such inserts is that almost all suitable materials have a refractive index significantly greater than the 1.376 refractive index of the stromal collagen of the cornea. This mismatch can result in unwanted reflective surfaces that may interfere with vision. Additional complications that may arise from a lack of biocompatibility include stromal melting and segment extrusion. Moreover, the commercially available ring segments are currently fixed in arc length, width, inner and outer diameter. The only variable is the thickness; thus, the procedure is not customizable to any great degree of precision.

Corneal transplants are usually reserved for the most severe corneal ectasias. In, for instance, treating severe keratoconus, both full and partial thickness transplants are used. The latter is also known as deep anterior lamellar keratoplasty (DALK). In DALK, the front and middle layers of the cornea are removed and replaced with suitably prepared donor corneal tissue.

Donor tissue preparation is usually performed by eye banks. Preparation for DALK typically consists of first stripping off the Descemet membrane (DM) and endothelium. A graft is then punched out from the endothelial side with a circular, standard punch, approximately 8-9 mm in diameter. The denuded and punched-out corneal stroma graft is then transplanted onto the recipient.

Despite good long-term graft survival, conventional corneal transplantation can be associated with many complications including graft rejection and infection.

Work has been reported on stromal lenticule addition keratoplasty (SLAK) in which patients with advanced keratoconus underwent implantation with a negative meniscus shaped intrastromal lenticule into a pocket within their corneal stroma. This procedure is discussed in, for instance, the article "Epithelial and stromal remodelling following femtosecond laser-assisted stromal lenticule addition keratoplasty (SLAK) for keratoconus" by Nubile et al., Sci Rep 11, 2293 (2021) the contents of which are hereby incorporated by reference.

However, limited work has been done on optimizing the shape of the intrastromal corneal implants to most appropriately ameliorate the various ectatic corneal disorders.

The relevant prior art also includes:

U.S. Pat. No. 8,394,140 granted to Chapoy et al. on Mar. 12, 2013, entitled "Pre-formed intrastromal corneal insert for corneal abnormalities or dystrophies". This patent describes the used of biocompatible polymer inserts to adjust corneal curvature.

Biocompatible polymers typically have an index of refraction significantly higher than the 1.376 of the cornea. Poly(methyl methacrylate) (PMMA) has been recognized as an excellent optical polymer for use in optical fibers, optical disks, and lenses. However, the refractive index of PMMA is limited to 1.49. Care has to be taken in shaping PMMA inserts to avoid unwanted reflections caused by the mismatched refractive indices that may interfere with vision.

U.S. Pat. No. 8,409,177 granted to Lai Apr. 2, 2013, entitled "Intrastromal refractive surgery by inducing shape change of the cornea". The pattern specification describes using a laser-ablation created intrastromal pocket which may be filled with a polymerizable fluid that is then cured.

Biocompatible polymerizable fluids typically also have an index of refraction significantly more the 1.376 typical of the cornea. The mismatched refractive indices may result in unwanted reflections and local focusing or defocusing that may interfere with vision.

U.S. Pat. No. 9,931,199 granted to Albertazzi on Apr. 3, 2018, entitled "Methods and apparatus for treating keratoconus" that describes a processing module that uses eye topography data to provide a surgical plan based on existing manufacture's available intrastromal corneal ring segments (ICRS).

Various implementations are known in the art but fail to address all of the problems solved by the invention described herein. Various embodiments of this invention are illustrated in the accompanying drawings and will be described in more detail herein below.

BRIEF SUMMARY OF THE INVENTION

Inventive methods for the amelioration of ectatic corneal disorders are disclosed. Corneal ectatic disorders may be a result of the thinning of the cornea that may become distorted and, therefore, adversely affect a patient's vision. They include diagnosis such as, but not limited to, keratoglobus, pellucid marginal degeneration, keratoconus, and forms of astigmatism, including irregular astigmatism.

As part of an assessment of the severity of a patient's disorder, one or more corneal maps of the patent's cornea may be obtained. These maps may be, but are not limited to, tomographic, topographic, or elevation maps, or some combination thereof. These maps may be used, for instance, to locate a cone of a keratoconus, and, to quantify a maximum keratometry of the patient's cornea.

In a preferred embodiment, the corneal maps of a patient exhibiting an ectatic or irregular disorder may be created using methods such as, but not limited to, computerized corneal topography and corneal tomography. The information derived from these maps, such as, but not limited to, the maximum keratometry and various iso-deviation contours, may then be used to calculate an appropriate three-dimensional shape of a corneal augmentation suitable for ameliorating the ectatic or irregular disorder. The ideal shape of the corneal augmentation may, for instance, be one that restores the patient's cornea to an ideal cornea, i.e., a portion of spheroid having a refractive power in the range of 30 to 50 diopters with an eccentricity ranging from −2 to +2.

A corneal template may be obtained as, for instance, a corneal autograft, a corneal allograft, a corneal xenograft, or as manufactured corneal tissue, or some combination thereof.

This corneal template may be treated for a number of purposes such as, but not limited to, to improve its biocompatibility, to maintain its clarity, and to increase its biomechanical strength.

This corneal template may be formed into a corneal augmentation of the desired three-dimensional shape using, for instance, a computer guided femtosecond or an excimer laser, or a combination thereof.

The cornea may then be augmented with the corneal augmentation either by inlaying it or overlaying it.

In the inlay procedure, a patient's cornea exhibiting an ectatic disorder may be prepared by creating an intra-corneal cavity using, for instance, a femtosecond laser. The intra-corneal cavity may be a space such as, but not limited to, a channel or a pocket with an appropriate opening for insertion of the augmentation. The corneal augmentation may then be inserted into the intra-corneal cavity, thereby augmenting the patient's cornea, and improving the patient's vision by improving the shape and optical performance of their cornea.

In the onlay procedure, the patient's cornea exhibiting an ectatic disorder may be prepared by first removing a region of epithelial tissue from the cornea. A surface chamfer may then be created on a periphery of the region of removed epithelial tissue using, for instance, a femtosecond laser. The corneal augmentation may then be augmented onto the patient's cornea and initially held in place by, for instance, inserting a tapered, or chamfered, edge of the corneal augmentation into the chamfer of the epithelial tissue. This may maintain the onlay in place while the epithelial tissue grows over the onlay. Surgical glues or sutures may also or instead be used for this temporary holding. Epithelial regrowth may take a few days to a week, during which time the patient's cornea may be protected by a surgical contact lens. Once in place, the onlay may improve the patient's vision by improving the optical performance of their cornea.

The inlay and onlay corneal augmentation procedures may themselves be sufficient to ameliorate the abnormality, or ectatic corneal disorder. However, they may also or instead be a first step, and may be followed by a post-augmentation further reshaping of the cornea. The post-operative further reshaping of the corneal augmentation may, for instance, be a surgery such as, but not limited to, a photorefractive keratectomy (PRK) surgery and a photo-therapeutic keratectomy (PTK).

Therefore, the present invention succeeds in conferring the following, and others not mentioned, desirable and useful benefits and objectives.

It is an object of the present invention to provide a method of ameliorating ectatic corneal disorders that is less invasive than alternative treatments such as, but not limited to, corneal transplants.

BRIEF DESCRIPTION OF THE SEVERAL VIEWS OF THE DRAWINGS

FIG. 1 A shows a schematic cross-section of a normally functioning human eye.

FIG. 1 B shows a schematic cross-section of a human eye exhibiting an abnormality of the cornea.

FIG. 2 A shows a schematic cross-section of a cornea having two intra-stromal cavities in preparation for having corneal augmentations as inlays.

FIG. 2 B shows a schematic cross-section of a cornea having two intra-stromal cavities.

FIG. 2 C shows a schematic cross-section of a cornea having two intra-stromal corneal augmentations as an inlays.

FIG. 3 A shows a schematic cross-section of a cornea exhibiting keratoconus.

FIG. 3 B shows a schematic cross-section of a cornea prepared to receive a corneal augmentation as an onlay.

FIG. 3 C shows a schematic cross-section of a cornea augmented with a corneal augmentation as an onlay.

FIG. 3 D shows a schematic cross-section of a cornea augmented with a corneal onlay after regrowth of the epithelial tissue.

FIG. 5 A shows a plan view of a doughnut shaped corneal template.

FIG. 5 B shows a plan view of two segments cut from a doughnut shaped corneal template.

FIG. 5 C shows a cross-sectional view of a segment cut from a doughnut shaped corneal template.

FIG. 6 A shows a plan view of a tangential map of a cornea exhibiting keratoconus.

FIG. 6 B shows a schematic plan view of doughnut segment corneal augmentations located relative to a tangential map of a cornea exhibiting keratoconus.

FIG. 7 A shows schematic rendering of an elevation map of a cornea exhibiting keratoconus.

FIG. 7 B shows a schematic cross-section showing a surface of a cornea exhibiting keratoconus and a best fit sphere as a reference.

FIG. 7 C shows a schematic cross-section showing a surface of a cornea exhibiting keratoconus and an enhanced best fit sphere as a reference.

FIG. 8 A shows a schematic representation of an iris image superimposed on an elevation map.

FIG. 8 B shows a schematic representation of an elevation map showing a keratoconus circle and a 3-mm representation of a pupil.

FIG. 10 A shows a schematic plan view of a corneal augmentation.

FIG. 10 B shows a schematic cross-sectional view of a corneal augmentation.

DETAILED DESCRIPTION OF THE INVENTION

The preferred embodiments of the present invention will now be described with reference to the drawings. Identical elements in the various figures are identified, in so far as possible, with the same reference numerals. The embodiments that are described in detail are provided by way of explanation of the present invention, which is not intended to be limited thereto. In fact, those of ordinary skill in the art may appreciate upon reading the present specification and viewing the present drawings that various modifications and variations can be made thereto.

Figure 1A:
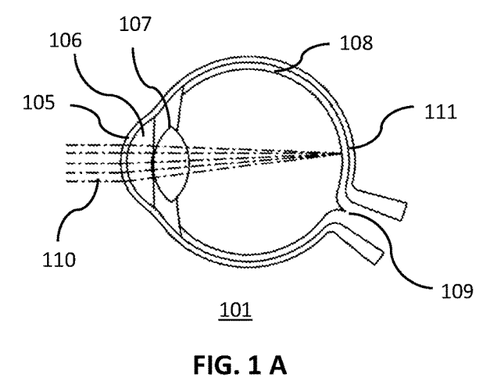

FIG. 1 A shows a schematic cross-section 101 of a normally functioning human eye.

In a normally functioning human eye, an incoming, parallel beam of light 110 may be light correctly focused 111 onto the retina 108 by the combined action of a lens 107 and a cornea 105. The image created on the retina 108 may then be transmitted to the brain via the optic nerve 109. The anterior cavity 106 is typically filled with a clear fluid, the aqueous humor, and separates the cornea 105 from the lens 107.

Figure 1B:
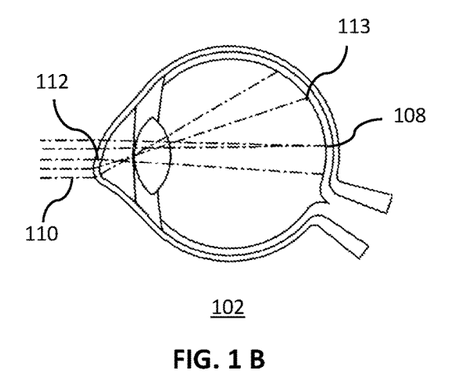

FIG. 1 B shows a schematic cross-section 102 of a human eye exhibiting an abnormality of the cornea that may be an ectatic disorder.

Corneal ectasia may be caused by the thinning and subsequent distortion of the cornea and may be manifested as a condition such as, but not limited to, keratoconus, pellucid marginal degeneration and keratoglobus. As a consequence of the thinning, the cornea 112 exhibiting an ectatic disorder may be distorted away from the normal spheroidal shape of a healthy cornea, thereby impairing its optical performance. For instance, only a small fraction of an incoming, parallel beam of light 110 may be correctly focused on the retina 108, while the remainder of the light 113 may not brought to a correct focus on the retina.

Figure 2A:
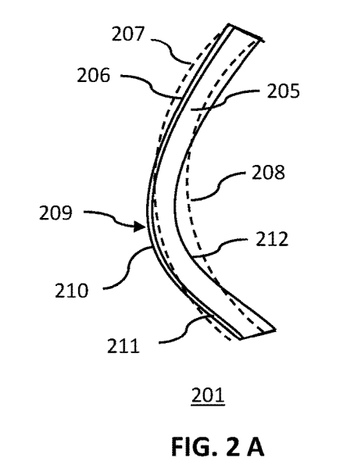

FIG. 2 A shows a schematic cross-section of a cornea exhibiting an ectatic disorder.

As shown, the cornea may be exhibiting keratoconus 209 in which a portion of the cornea may assume an irregular optical surface that may sometimes be referred to as a cone.

The degree or severity of the keratoconus 209 may be characterized by the deviation of the cornea from an optimal optical structure. Such an optimal optical structure may, for instance, be an ideal cornea, i.e., a portion of spheroid having a refractive power in the range of 30 to 50 diopters with an eccentricity ranging from −2 to +2. The severity of the condition may be quantified by a number of clinical variables. These variables may, for instance, include the following:

1: The maximum keratometry or K-max. This may be measured as the maximum deviation of the cornea from the ideal and may determine the severity of the keratoconus. A measure of the maximum keratometry 210 may, for instance, be obtained using an instrument such as, but not limited to, a Pentacam™ manufactured by OCULUS Optikgerate GmbH in Wetzlar, Germany. The measurement may be quantified in diopters or as a deviation in m of the anterior surface of the cornea 211 from a best fit sphere 207 for the anterior surface of cornea, or as a deviation in m of the posterior surface of the cornea 212 from a best fit sphere 208 for posterior surface of cornea, or a combination thereof.

2: An estimate of the corneal curvature over the visual axis. This may be obtained from refraction measurements of the degree of myopia and hyperopia caused by the deformed cornea. The myopia may be measured assuming the visual axis passes through the steepest part of the deformed cornea, i.e., the cone of the keratoconus. The hyperopia may be measured by assuming the visual axis passes through the flatter part of the deformed cornea. Both of this refraction measurements may also be calculated from data obtained using corneal tomography or topography as performed by an instrument such as, but not limited to, the aforementioned Pentacam™.

3: The location of the so-called cone of the keratoconus, particularly the location of the cone relative to the pupil. This clinical location may be obtained by overlying a map of the cornea with an iris image. A map of the cornea may show the local focusing power of the cornea and may be obtained with an instrument such as, but not limited to, a Pentacam™. Optical topography and tomography instruments such as the Pentacam™ typically have an iris camera that may provide a suitable iris image.

4: The diameter of the cone on the cornea. This may, for instance, be obtained from an elevation map that may compare the local height of the cornea to a reference surface such as, but not limited to, a best fit sphere. For instance, a best fit sphere 207 for the anterior surface of the cornea may be compared to the anterior surface of the cornea 211 to produce an elevation map. A roughly circular patch may then become apparent as the boundary at which the cornea starts to deviate significantly from the best fit sphere. The diameter of a best fit circle to this region may then be deemed to be the diameter of the cone. The same calculation may be done comparing the posterior surface of the cornea 212 to a best fit sphere 208 for the posterior surface of the cornea.

Based on the clinical measurements of the severity, location and diameter of the keratoconus cone, a clinician may then determine a best course of treatment. The treatment may, for instance, be a multistep treatment in which a cornea inlay or onlay is added to the patent's cornea, followed later by laser reshaping of the thickened cornea.

Figure 2B:
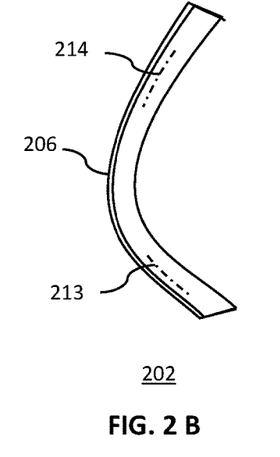

FIG. 2 B shows a schematic cross-section 202 of a cornea having two intra-stromal cavities in preparation for having corneal augmentations as inlays.

Depending on factors such as, but not limited to, the severity and location of the disorder, a clinician may opt to treat it with a single inlay, or with multiple inlays.

The intra-stromal cavities 213 and 214 may be created in the corneal stroma 205 using any suitable surgical means though the use of a femtosecond laser may be preferred as the photodissociation incisions produced by a femtosecond laser cause minimal damage to surrounding tissue. The intra-stromal cavities 213 and 214, or pockets, may create a space appropriately sized and shaped to each receive a corneal augmentation. A typical cornea is about 540 μm+/− 30 μm thick though, with ectasia, the thickness in regions may be as little as 300 μm. An optimal depth for locating the intra-stromal cavities may be between 90 μm from the epithelial tissue and at least 100 μm above the posterior surface of the cornea, or Descemet's layer. Preferably, the location may be as close to the 90 μm limit as possible. There may be entrances to the intra-stromal cavities 213 and 214 that pierce the epithelial tissue 206 and allow for the insertion of the corneal augmentations.

Figure 2C:
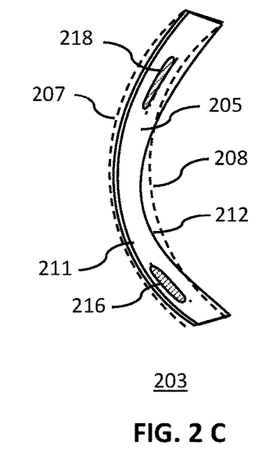

FIG. 2 C shows a schematic cross-section 202 of a cornea having two intra-stromal corneal augmentations 216 and 218 as inlays.

The corneal augmentations 216 and 218 been placed, or inlayed, into the intra-stromal cavities 213 and 214 thereby ameliorating the keratoconus by strengthening and reshaping the cornea. In particular, both the anterior surface of the cornea 211 and the posterior surface of the cornea 212 are now more closely aligned to the best fit sphere 207 for anterior surface of cornea and the best fit sphere 208 for posterior surface of cornea respectively. The cornea may now more closely approximates an ideal optical structure, thereby improving its optical performance and the patient's vision.

Figure 3:
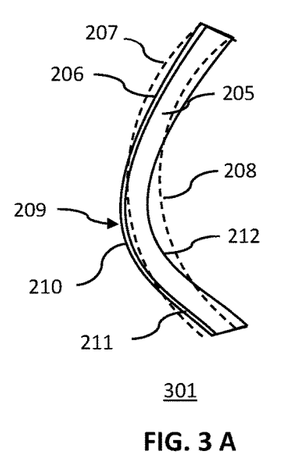

FIG. 3 A shows a schematic cross-section 301 of a cornea exhibiting keratoconus.

As in FIG. 2 A, the cornea may be exhibiting keratoconus 209 having a maximum keratometry 210 in a vicinity of the thinnest part of the corneal stroma 205. The deformation of the cornea may be measured as a deviation of the anterior surface of the cornea 211 from a best fit sphere 207 for anterior surface of cornea. An almost identical pattern may be seen in the deviation of the posterior surface of the cornea 212 from a best fit sphere 208 for posterior surface of cornea. Both these deviations may be mapped and visualized as elevation maps by means of tomography or topography using an instrument such as, but not limited to, the Pentacam™ mentioned above.

FIG. 3 B shows a schematic cross-section 302 of a cornea prepared to receive two corneal augmentations as onlays. A first surgical step in the onlay procedure may be to remove one or more regions 305 and 310 of epithelial tissue 206. This removal may be performed by any suitable surgical procedure, but the use of a femtosecond laser may be preferred as the photodissociation incisions produced by a femtosecond laser cause minimal damage to surrounding tissue. The regions 305 and 310 in which epithelial tissue is removed may typically on either side of the thinnest part of the corneal stroma 205.

In addition to removing the epithelial tissue, a surface chamfer 306 may be produce on a periphery of the region of removed epithelial tissue. This may also be done using a femtosecond laser and may serve to help secure the on-laid corneal augmentation.

FIG. 3 C shows a schematic cross-section 303 of a cornea augmented with two corneal augmentations 308 and 311 as onlays.

The corneal augmentations 308 and 311 may be placed over, or on-laid, over the regions in which epithelial tissue has been removed. The corneal augmentations may be held in place temporarily by having its outer periphery tucked under a surface chamfer 306 on the periphery of the region of removed epithelial tissue. The corneal augmentation may also or instead be temporarily held in place by surgical glue or sutures, or a combination thereof.

Figure 3D:
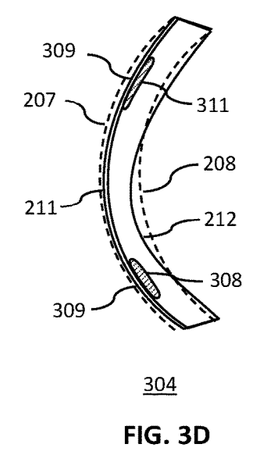

FIG. 3 D shows a schematic cross-section 304 of a cornea augmented with two corneal onlays after regrowth of the epithelial tissue 309.

Regrowth of the epithelial tissue may take approximately a few days to a week. During this period a patient may wear surgical contact lenses to protect the augmentation. As the epithelial tissue regrows, the corneal augmentations 308 may integrate with the corneal stroma 205 thereby strengthening and reshaping the cornea. In particular, both the anterior surface of the cornea 211 and the posterior surface of the cornea 212 may now be more closely aligned to the best fit sphere 207 for anterior surface of cornea and the best fit sphere 208 for posterior surface of cornea respectively. The cornea may now more closely approximate an ideal optical structure, thereby ameliorating the keratoconus. This may also improve the cornea's optical performance and the patient's vision.

Although the procedures detailed in FIGS. 2A-C and 3 A-D, are shown as having two corneal augmentations each, there are many occasions on which a single suitably shaped and placed corneal augmentation may prove as, or even more, effective in ameliorating the corneal abnormality.

The procedures detailed in FIGS. 2A-C and 3 A-D, i.e., inlay and onlay corneal augmentation, may themselves be sufficient to ameliorate the abnormality, or ectatic corneal disorder. However, they may also or instead be a first step, and may be followed by a post-augmentation further shaping of the corneal augmentation. The post-augmentation further shaping of the corneal augmentation may, for instance, be a surgery such as, but not limited to, a photorefractive keratectomy (PRK) surgery or a phototherapeutic keratectomy (PTK). Such surgeries may, for instance, be accomplished using a suitable laser such as, but not limited to, a femtosecond laser, or an Excimer laser, or a combination thereof.

Figure 4:
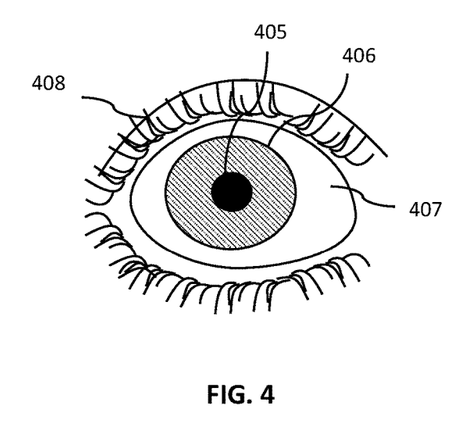
FIG. 4 shows a schematic plan view of a human eye.

FIG. 4 shows a schematic plan view 401 of a human eye. As shown, the eye typically consists of an eyeball 407 contained within a protective socket and surrounded by eyelashes 408. Components of the eye that participate in the imaging function of the eye include the iris 406 and the pupil 405. The pupil 405, for instance, is a variable aperture through which light rays pass to be imaged onto the retina at the rear of the eye.

Figure 5:
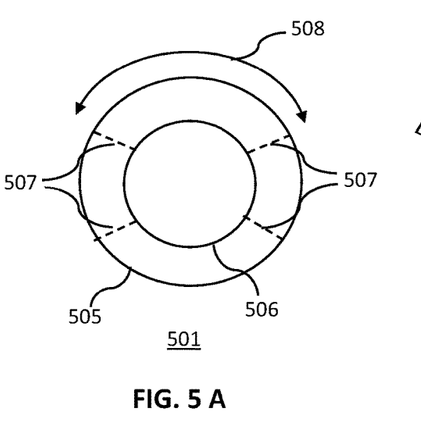

FIG. 5 A shows a plan view 501 of a doughnut shaped corneal template.

The initial corneal template, before being shaped into a doughnut, may have been obtained as any suitable material such as, but not limited to, as a corneal autograft, a corneal allograft, a corneal xenograft, a manufactured corneal tissue, or some combination thereof. In a preferred embodiment, the corneal template may be obtained from a donated human cornea, as prepared, and or preserved, by, for instance, a reputable eye bank such as, but not limited to, CorneaGen Inc., headquartered in Seattle, Wash., which is a subsidiary of SightLife, Inc, also headquartered in Seattle, Wash.

Such eye banks typically treat the corneal template for multiple purposes, such as but not limited to:

improve the biocompatibility of the corneal template by decellularization;

aid in preserving the corneal template by decontamination and sterilization;

maintain the clarity of the corneal template and minimize edmea by deturgessing agents; increase the biomechanical strength of the corneal template by the addition of stiffening agents;

improve the ease of performing the augmentation procedure by marking for orientation, and by suitable dying for visibility;

allow the corneal template and the corneal augmentation obtained from it to be kept at room temperature for reasonable lengths of time, typically up to two years, and, improve postoperative healing and prophylaxis by soaking in drugs, biologics, or regenerative therapies.

The initial corneal template may then be shaped into a doughnut, or ring shape, having a circular outer radius 505 and a circular inner radius 506. This shaping may, for instance, be done using a femtosecond laser. The doughnut, or ring shape, may have one or more lateral cuts 507 that may also be accomplished using a femtosecond laser. These lateral cuts may result in corneal segments having a required arc length 508.

The outer radius 505 may, for instance, be in a range of 7 to 9 mm, and is more preferably about 8 mm. The inner radius 506 of a doughnut shaped corneal template may be in a range of 3 to 5 mm and is more preferably about 4 mm.

FIG. 5 B shows a plan view 502 of two segments 509 and 510 cut from a doughnut shaped corneal template. Once trimmed to an appropriate thickness, these segments may then be suitable corneal augmentations. They may be used singly or in combination. Although FIG. 5 B shows two segments being cut from the doughnut, a single arc shaped segment having an arc length of greater than 180 degrees may instead be obtained from the doughnut.

FIG. 5 C shows a cross-sectional view 503 of a segment cut from a doughnut shaped corneal template. Once trimmed to an appropriate thickness, this segment may then be a suitable corneal augmentation.

A typical width 512 of a doughnut sector shaped corneal augmentation may be in a range of 3 to 5 mm and is more preferably about 4 mm.

A thickness 511 of a doughnut sector shaped corneal augmentation may depend on a severity of the corneal abnormality. The thickness 511 of the corneal augmentation may, for instance, be proportional to the maximum keratometry, a.k.a. the K-max, of the abnormality.

For instance, a satisfactory relationship between maximum thickness of the corneal augmentation and K-max has been found through experience to be that represented in Table 1.

TABLE 1

Maximum thickness of collagen augmentation in μm verses maximum keratometry measured in Diopters

| Tissue Thicknees (um) | Maximum Keratometry (Diopters) |
| --- | --- |
| 100-200 | 45-50 |
| 200-250 | 50-55 |
| 250-300 | 55-60 |
| 300-350 | 60-65 |
| 350-400 | 65-70 |
| 400-450 | 70-75 |
| 450-500 | >75 |

The values in Table 1 may be approximated by the equation:

$$t = 10 \times K\text{-max} - 300 \qquad (1)$$

where t represents the maximum thickness in m and K-max represents the maximum keratometry in diopters.

Figure 6:
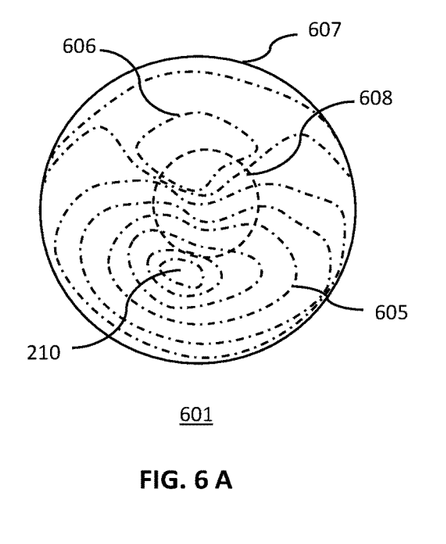

FIG. 6 A shows a plan view 601 of a tangential map of a cornea exhibiting keratoconus.

Data obtained in examining an eye using tomographic or topographic systems such as, but not limited to, a Pentacam™ may be displayed in a number of ways including, but not limited to, pachymetric maps that display the corneal thickness, axial and tangential maps that display local curvature of the cornea, and elevation maps that display the corneal surfaces with respect to a reference surface.

A tangential map is typically displayed in false color, with particular colors representing specific local powers of refraction. For instance, a iso-diopter line 605 of elevated power may be displayed in a warmer color tending to the red end of the spectrum, while a iso-diopter line 606 of diminished power may displayed in colder color tending to the blue end of the spectrum. A maximum keratometry 210 may, therefore, be displayed as a dark red. A typical tangential map may fill the circumference 607 of the cornea and be overlaid with a 3-mm circle 608 representative of the pupil of the eye.

FIG. 6 B shows a schematic plan view 602 of two doughnut segment corneal augmentations located relative to a tangential map of a cornea exhibiting keratoconus.

As shown in FIG. 6 B, a first corneal augmentation 609 may be located on one side of the maximum keratometry 210. The first corneal augmentation 609 may further be located so that an outer edge is, in part, a best fit to a first iso-diopter line 610 of elevated power, while an inner edge may be a best fit to a second iso-diopter line 611 of elevated power. The arc length of the first corneal augmentation 609 may also be constrained by the iso-power lines.

A second corneal augmentation 612, if deemed necessary for amelioration of the corneal disorder, may be located on the other side of the maximum keratometry 210. The second corneal augmentation 612 may further be located such that an outer edge may be, in part, a best fit to a first iso-diopter line 613 of diminished power, while an inner edge may be, in part, a best fit to a second iso-diopter line 614 of diminished power. The arc length of the second corneal augmentation 609 may also be constrained by the iso-power lines.

Figure 7:
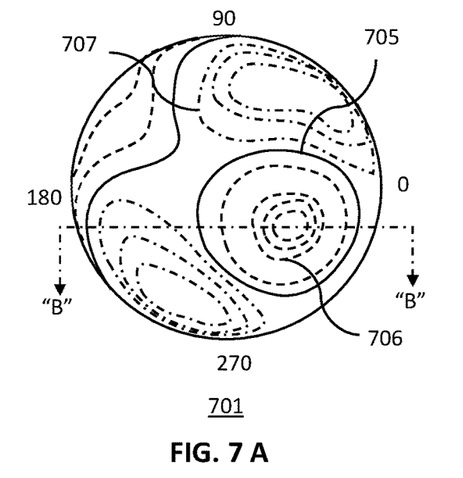

FIG. 7 A shows schematic rendering of an elevation map 701 of a cornea exhibiting keratoconus.

Data obtained in examining an eye using tomographic or topographic systems such as, but not limited to, a Pentacam™ may be displayed in a number of ways including, but not limited to, pachymetric maps that display the corneal thickness, axial and tangential maps that display local curvature of the cornea, and elevation maps that display the corneal surfaces with respect to a reference surface.

An elevation map is typically displayed in false color, with particular colors representing particular amounts of deviation of the corneal surface from a reference surface. In order to conform to patent office drawing requirements, the elevation map 701 has been shown with dotted lines representing iso-elevation lines, i.e., lines that would normally be displayed as a particular color. For instance, iso-elevation line 706 represents a particular amount of elevation of a corneal surface above a reference surface and would, by convention, normally be displayed by a warm color tending to the red end of the spectrum. The iso-elevation line 707 represents an elevation of a corneal surface below a reference surface and would normally be displayed by a cold color tending to the blue end of the spectrum. A zero iso-elevation line 705 would normally be displayed as a color in the yellow to green part of the spectrum.

The numbers 0, 90, 180 and 270 represent orientation in degrees as per ophthalmic convention.

FIG. 7 B shows a schematic cross-section 502 showing a surface of a cornea exhibiting keratoconus 710 and a best fit sphere 709 as a reference.

The cross-section 702 is taken on the line "BB" in FIG. 7 A. The best fit sphere 709 is the best fit sphere to the entire corneal surface 708 that may include data points from the region of keratoconus 710. The elevation map shown in FIG.

7A may represent the difference between the best fit sphere 709 and one of the surfaces of the cornea. As a point of reference, in normal eyes the anterior elevations are typically in a range 1.63+/−1.4 μm. In a patient with keratoconus, the anterior elevations may be the range of 20.9+/−21.9 μm. Best fit spheres typically have a radius in a range of 6.5+/−2 mm.

FIG. 7C shows a schematic cross-section 703 showing a surface of a cornea exhibiting keratoconus 710 and an enhanced best fit sphere 711 as a reference surface.

The enhanced best fit sphere 711 may be calculated using data from the corneal surface 708 but excluding data from the region 712 that may represent the region most affected by the keratoconus 710.

Figure 8:
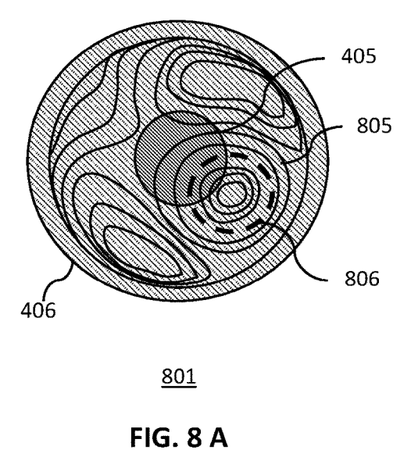

FIG. 8A shows a schematic representation 801 of an iris image 406 superimposed on an elevation map.

By having the image of the iris 406 superimposed on the elevation map, it may be possible to determine the relative position of the pupil 405 and a circle 806 defining a diameter of a keratoconus. Also shown are the other iso-elevation lines 805.

FIG. 8B shows a schematic representation 802 of an elevation map having iso-elevation lines 805. Also shown are a keratoconus circle 806 and a 3 mm circle 807 that may represent the position of the pupil. The circle 806 defining a diameter of a keratoconus may, for instance, be a best fit circle to the iso-elevation line at which the surface of the cornea starts to deviate significantly from the best fit sphere. The diameter of a best fit circle may be deemed to be the diameter of the cone of the keratoconus.

Also shown is a vector 810 representing a distance and direction between the center of the pupil and the center 808 of the keratoconus maximum.

Figure 9:
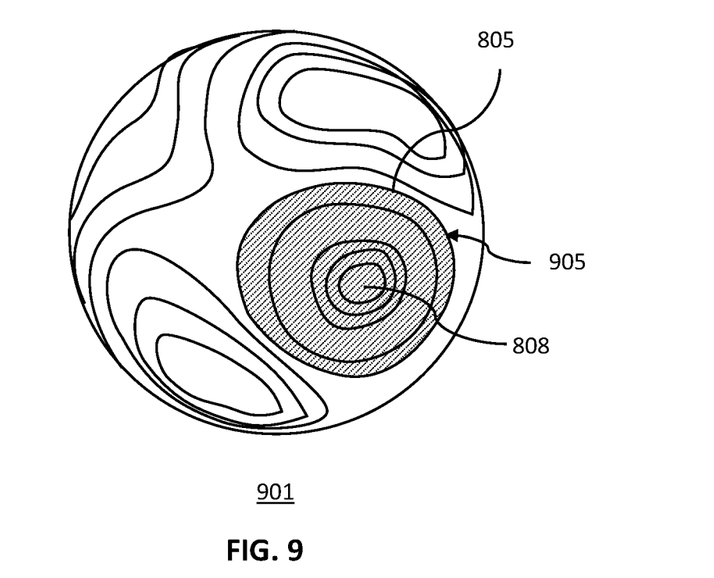
FIG. 9 shows a schematic representation of a corneal augmentation shaped to have a plan projection matching an iso-elevation line.

FIG. 9 shows a schematic representation 901 of a corneal augmentation 905 shaped to have a plan projection matching an iso-elevation line 805 of an elevation map of a cornea. The corneal augmentation 905 may be roughly centered over the keratoconus maximum 808.

The selection of an appropriate iso-elevation line may define the peripheral shape of a plan projection of the corneal augmentation 905 and its maximum thickness may be determined by the severity of the keratoconus as measured by the value of the keratoconus maximum, a.k.a. K-max.

For instance, a satisfactory relationship between maximum thickness of the corneal augmentation and K-max has been found through experience to be that represented in Table 1 shown above, and may be approximated by Equation 1, shown above.

Figure 10:
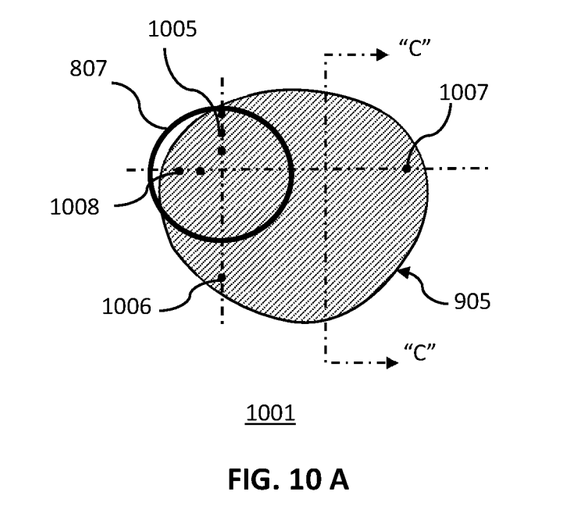

FIG. 10A shows a schematic plan view 1001 of a corneal augmentation 905.

Although the corneal augmentation 905 shown in the figure has a plan projection matching an iso-elevation line of an elevation map of a cornea, one of ordinary skill in the art may appreciate that the plan projection may be any suitable plan projection such as, but not limited to, a polygon that may be a best fit, in part, to the iso-elevation line, a lenticule that may be a best fit, in part, to the iso-elevation line, a circle that may be a best fit, in part, to the iso-elevation line, a free-form curve that may be a best fit, in part, to the iso-elevation line, a crescent shape may be a best fit, in part, to the iso-elevation line, or some combination thereof.

The corneal augmentation 905 may have been created from a corneal template that may then have been transformed into to the appropriate three-dimensional shape using any suitable material removal or cutting techniques such as, but not limited to, a computer guided femtosecond laser, or a computer guided Excimer laser, or some combination thereof.

The corneal template may have been obtained as any suitable material as discussed in more detail previously.

FIG. 10A also shows the corneal augmentation 905 marked with placement indicia. The indicia may for instance be small holes punched in the corneal augmentation and arranged to provide both positioning and orientation information. For instance, a first placement indicium 1005 marking a 90-degree alignment may have three small holes that indicate placement vertically up. A second placement indicium 1006 marking a 270-degree alignment may have only a single hole, that indicates placement vertically down. When an imaginary line is drawn from first indicium to the second, the line may pass through the center of the 3 mm diameter 807 circle representing a pupil. In actual placement, when correctly placed, the imaginary line may pass through the center of the patient's pupil. Similarly, a third placement indicium 1008 marking a 180-degree alignment may have two holes, while a fourth placement indicium 1007 marking a 0-degree alignment that may have a single hole. When an imaginary line is draw from the third to the fourth placement indicium to it may pass horizontally thorough the center of the pupil when the augmentation is correctly positioned and oriented.

One of ordinary skill in the art may appreciate that although the placement indicia have been described in terms of punched holes any suitable marking system may be used including, but are not limited to, colored dyes, small incisions, or some combination thereof.

FIG. 10B shows a schematic cross-sectional view 1002 of a corneal augmentation 905. As shown, the corneal augmentation 905 has a crescent shaped cross-section with a maximum thickness 1009 that may be proportional to the maximum keratometry, or K-max, and may be determined by Equation 1, or Table 1. If the corneal augmentation 905 is intended for use as an onlay, the posterior surface 1010 may be shaped to be a match to the anterior surface of the cornea in the region where the onlay augmentation is intended to be placed.

Although the augmentation cross-section is shown as a crescent shape, one of ordinary skill in the art may realize that it may be of any suitable shape such as, but not limited to, a rectangle, an oval, a sphere, a portion of a sphere, or some combination thereof.

Figure 11:
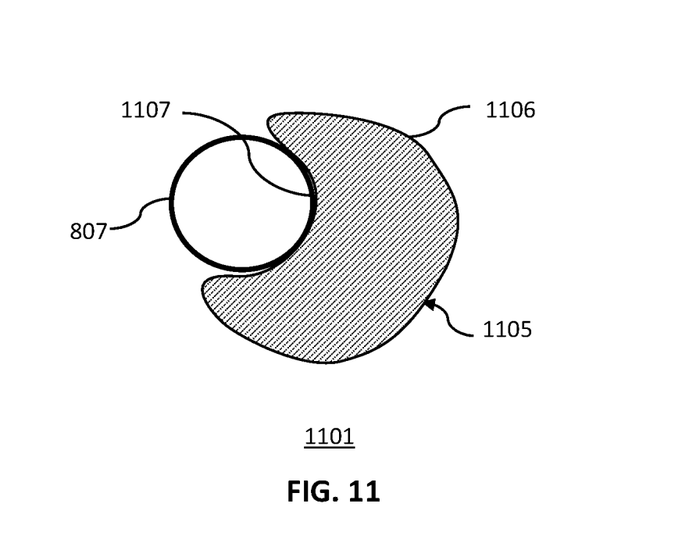
FIG. 11 shows a schematic plan view of a corneal augmentation shaped to avoid covering the pupil.

FIG. 11 shows a schematic plan view 1101 of a corneal augmentation 1105 shaped to avoid covering the pupil.

The plan projection of the corneal augmentation 1105 shaped to avoid covering the pupil may have a portion 1106 of the periphery that may be fitted to an iso-elevation line 805, and a portion 1107 of the periphery to a 3-mm diameter 807 circle representing a position of a pupil. A reason for making such an augmentation may be to avoid the augmentation interrupting a patient's line of sight as the surface of the augmentation may not be sufficiently smooth and may adversely affect the patient's vision.

Although the plan projection of the augmentation shown in FIG. 11 is drawn as a partial best fit to an iso-elevation line and a partial best fit to a circle, one of ordinary skill in the art may appreciate that the plan projection may be any suitable shape such as, but not limited to, a crescent, or an arc, or a free form curve, or some combination thereof that may also be partial best fits to an iso-elevation line and/or to a circle representing the pupil.

Figure 12:
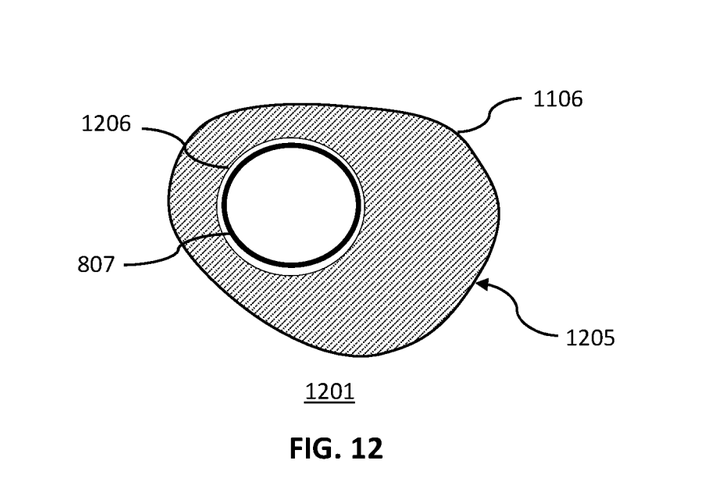
FIG. 12 shows a schematic plan view of a corneal augmentation having a doughnut shape to avoid covering the pupil.

FIG. 12 shows a schematic plan view 1201 of a corneal augmentation 1205 having a doughnut shape to avoid covering the pupil.

The cut-out's purpose may be to avoid obscuring a line of sight through the cornea as the surface of the augmentation may not be sufficiently smooth to ensure sufficiently unperturbed transmission of light.

An outer periphery of the plan projection of a corneal augmentation 1205 having a doughnut shape to avoid covering the pupil may be a free form best fit to an iso-elevation line, or it may be any suitable geometric shape such as, but not limited to, a polygon or a circle, that may also be, in part, a best fit to a selected iso-elevation line. The corneal augmentation may also have a cut-out 1206 shaped and sized to avoid obscuring the pupil, as represented by the 3-mm diameter 807. The plan projection of this cut-out may be a circle that encompasses the 3-mm diameter 807 circle, or it may be a best fit to it. One of ordinary skill in the art may appreciate that the plan projection of the cut-out may also be any suitable free form shape, or polygon, or a combination thereof that may also encompass or be a best fit to the 3-mm diameter 807 circle representing a pupil.

Figure 13:
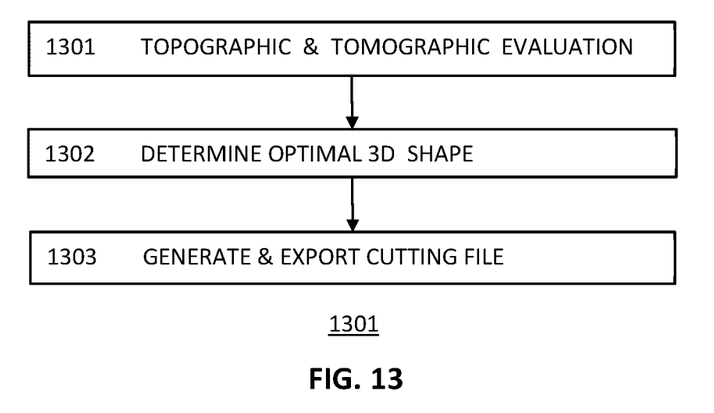
FIG. 13 shows a flow diagram showing representative steps in the automated determination of a three-dimensional shape of a corneal augmentation.

FIG. 13 shows a flow diagram 1301 showing representative steps in the automated determination of a three-dimensional shape of a corneal augmentation.

In Step 1301 "TOPOGRAPHIC & TOMOGRAPHIC EVALUATION" a patient's cornea may be examined using a suitable computer controlled topographic or tomographic instrument such as, but not limited to, a Pentacam™.

In Step 1302 "DETERMINE OPTIMAL 3D SHAPE", a suitably programmed digital processor may take the data obtained in the previous step and calculate an optimal three-dimensional shape for a corneal augmentation to ameliorate a patient's corneal abnormality. This calculation may, for instance, include some or all of the concepts discussed above such as, but not limited to, a relationship between the maximum keratometry and the suitable thickness of the augmentation and having the periphery of the augmentation be, in part, a best fit to one or more iso-deviation in elevation, or iso-power lines. The calculation may also take into account other data that may be provided such as, but not limited to, properties of a patent's other eye or cornea.

In Step 1303 "GENERATE & EXPORT CUTTING FILE" the suitably programmed digital processor may convert the optimal three-dimensional shape into a form suitable for use by computer controlled micro-precision shaping machine. This may result in a cutting file formatted in a suitable CAD format. Suitable CAD format file types include, but are not limited to, the well-known STEP and STL file formats.

Figure 14:
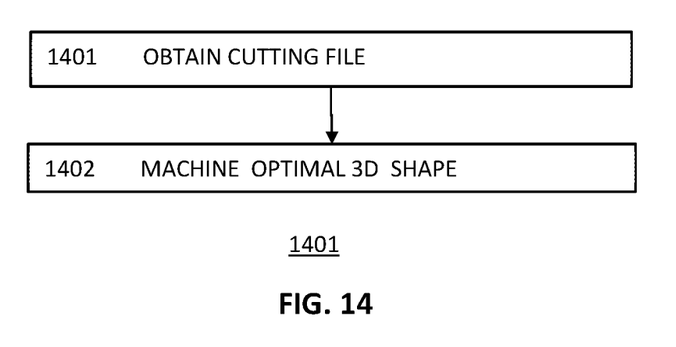
FIG. 14 shows a flow diagram showing representative steps in the automated fabrication of a corneal augmentation.

FIG. 14 shows a flow diagram 1401 showing representative steps in the automated fabrication of a corneal augmentation.

In Step 1401 "OBTAIN CUTTING FILE" the CAD cutting file generated in the process described above may be input to a suitable a computer controlled micro-precision shaping machine. The micro-precision shaping machine may include a femtosecond laser and a computer controlled micro-precision XYZ stage. Such a stage may, for instance, be constructed from components supplied by, for instance, Thorlabs of Newton, N.J. The components may, for instance, include their MLS203-1—Fast XY Scanning Stage and their MZS500-E Z-Axis Piezo Stage.

In Step 1402 "MACHINE OPTIMAL 3D SHAPE", a corneal template mounted on the computer controlled micro-precision XYZ stage the may be translated past the focal point of a suitably powerful femtosecond laser in order to produce the corneal augmentation. This process may be analogous to 3D printing in reverse, i.e., successive layers of material may be removed instead of being added.

One of ordinary skill in the art may appreciate that although the invention has been described primarily with respect to keratoconus, the inventive methods may be used, or adapted for use, for a variety of other corneal ectasia such as, but not limited to, keratoglobus, pellucid marginal degeneration, posterior keratoconus, post-LASIK ectasia, Terrien's marginal degeneration, and irregular astigmatism.

One of ordinary skill in the art may further appreciate that although the invention has been described primarily through reference to elevation maps, the inventive steps may also or instead be implemented through the use of other corneal maps such as, but not limited to, pachymetric maps that display the corneal thickness, and axial and tangential maps that display local curvature of the cornea.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed:

1. A method for the amelioration of an abnormality of a cornea, comprising:

determining a measure of severity of said abnormality of said cornea;

creating a corneal map of said cornea quantifying a deviation of said abnormal cornea from an optimal corneal shape;

calculating, using said corneal map and said measure of severity, an appropriate three-dimensional shape of a corneal augmentation to ameliorate said disorder of said cornea;

producing said corneal augmentation using a cornel template comprised of corneal tissue and having said appropriate three-dimensional shape; and, augmenting said cornea with said corneal augmentation.

2. The method of claim 1, wherein, said producing said corneal augmentation further comprises obtaining said corneal template from a source other than said cornea being treated by means of one of a corneal allograft, and a corneal xenograft; and, prior to augmentation, shaping said corneal template to create said appropriate three-dimensional shape of said corneal augmentation.

3. The method of claim 2, wherein, said abnormality of said cornea is keratoconus; said measure of severity is a maximum keratometry (K-max); and said corneal map is obtained using corneal tomography or corneal topography.

4. The method of claim 3, wherein, said appropriate three-dimensional shape is a sector of a doughnut shape.

5. The method of claim 4 wherein said sector is cut from a doughnut shape having an inner radius in a range of 3 to 5 mm, and outer radius in a range of 7 to 9 mm, and a uniform thickness determined using the equation: $t = 10 \times K\text{-max} - 300$, where t is the thickness in m, and K-max is the maximum keratometry measured in diopters.

6. The method of claim 3, wherein, said corneal map is an elevation map and said appropriate three-dimensional shape of said corneal augmentation has a plan projection that is a curve that is, in part, a best fit to an iso-elevation line of said elevation map.

7. The method of claim 6, wherein, a maximum thickness of said corneal augmentation is proportional to said maximum keratometry of said keratoconus.

8. The method of claim 7, wherein, said maximum thickness of said corneal augmentation is determined using the equation: $t=10 \times K\text{-max}-300$, where t represents the maximum thickness in m, and K-max represents the maximum keratometry measured in diopters.

9. The method of claim 3, wherein, said appropriate three-dimensional shape is determined automatically, using data comprising said corneal map and said measure of severity, by a suitably programmed digital processor, and wherein a cutting file is generated by said suitably programmed digital processor, said cutting file containing instructions readable by a computer-controlled femtosecond laser to form said corneal augmentation.

10. The method of claim 3, wherein, said corneal map is an elevation map and said appropriate three-dimensional shape of said corneal augmentation has a plan projection that is one of a polygon, a lenticule, a doughnut, a crescent and an arc; and, said plan projection is, in part, a best fit to an iso-elevation line of said elevation map.

11. The method of claim 10, wherein, said plan projection of said corneal augmentation further comprises a cut-out to avoid obscuring a line of sight through said cornea.

12. The method of claim 11, wherein, said corneal augmentation further comprises alignment indicia to aid in the correct placement of said corneal augmentation during augmentation.

13. The method of claim 2, wherein, said corneal augmentation is an inlay; and, augmenting said cornea with said corneal augmentation further comprises creating an intra-stromal cavity, said cavity being sized and shaped to accommodate said inlay.

14. The method of claim 13, wherein, said intra-stromal cavity is created using a femto-second layer.

15. The method of claim 2, wherein, said corneal augmentation is an onlay placed external to said cornea being treated; and, augmenting said cornea with said corneal augmentation further comprises first removing a contiguous region of epithelial tissue corresponding in area to a plan projection of said corneal augmentation.

16. The method of claim 15, wherein, said removing a region of epithelial tissue is accomplished using a femto-second laser.

17. The method of claim 16, wherein, said augmenting further comprises temporarily retaining said onlays on said cornea using a surface chamfer of epithelial tissue on a periphery of said removed region of epithelial tissue.

18. The method of claim 2 further comprising a post-augmentation reshaping of the cornea.

19. The method of claim 18, wherein, said post-operative reshaping of the cornea comprises photorefractive keratectomy (PRK) surgery.

20. The method of claim 19, wherein, said post-operative reshaping of the cornea comprises using an excimer laser.

* * * * *